United States Patent
Weiser (10) Patent No.: US 10,254,210 B2
(45) Date of Patent: Apr. 9, 2019

(54) FLOW THROUGH DEBRIS SENSOR

(71) Applicant: Eaton Corporation, Cleveland, OH (US)

(72) Inventor: David Weiser, Philadelphia, PA (US)

(73) Assignee: Eaton Intelligent Power Limited, Dublin (IE)

( * ) Notice: Subject to any disclaimer, the term of this patent is extended or adjusted under 35 U.S.C. 154(b) by 69 days.

(21) Appl. No.: 15/117,915

(22) PCT Filed: Mar. 4, 2015

(86) PCT No.: PCT/US2015/018723
§ 371 (c)(1),
(2) Date: Aug. 10, 2016

(87) PCT Pub. No.: WO2015/134602
PCT Pub. Date: Sep. 11, 2015

(65) Prior Publication Data
US 2016/0370275 A1    Dec. 22, 2016

Related U.S. Application Data

(60) Provisional application No. 61/947,710, filed on Mar. 4, 2014.

(51) Int. Cl.
| | |
|---|---|
| *G01N 15/06* | (2006.01) |
| *G01N 27/74* | (2006.01) |
| *F16N 29/04* | (2006.01) |
| *G01N 33/28* | (2006.01) |

(Continued)

(52) U.S. Cl.
CPC ........ *G01N 15/0656* (2013.01); *F16N 29/00* (2013.01); *F16N 29/04* (2013.01); *G01N 27/74* (2013.01); *G01N 33/28* (2013.01); *G01N 33/2858* (2013.01); *F16N 2200/04* (2013.01); *F16N 2250/32* (2013.01); *F16N 2250/52* (2013.01); *G01N 2015/0053* (2013.01)

(58) Field of Classification Search
None
See application file for complete search history.

(56) References Cited

U.S. PATENT DOCUMENTS 3,432,750 A * 3/1969 Botstiber ........... G01N 15/0656
                                                200/61.09
4,731,578 A   3/1988 Tsaprazis
(Continued)

OTHER PUBLICATIONS

European Patent Office, International Search Report and Written Opinion issued in corresponding International Application No. PCT/US2015/018723. dated May 15, 2015.

*Primary Examiner* — Jermele M Hollington
*Assistant Examiner* — Suresh K Rajputra
(74) *Attorney, Agent, or Firm* — Fishman Stewart PLLC (57) ABSTRACT

A debris sensor may include a body including a first end and a second end, a ferrous particle sensor connected to the body, and a magnetic chip collector connected to the body at a position closer to the second end than the ferrous particle sensor. A plurality of magnets may be disposed closer to the second end than the magnetic chip collector. A non-ferrous particle sensor may be connected to the body and the non-ferrous particle sensor may be disposed closer to the second end than the plurality of magnets.

22 Claims, 6 Drawing Sheets

(51) Int. Cl.
  *F16N 29/00* (2006.01)
  *G01N 15/00* (2006.01)

(56) References Cited

U.S. PATENT DOCUMENTS

| | | | |
|---|---|---|---|
| 4,935,122 A * | 6/1990 | Dreyfuss | B03C 1/23 |
| | | | 209/208 |
| 5,028,318 A | 7/1991 | Aslin | |
| 5,061,364 A | 10/1991 | Metala et al. | |
| 5,708,198 A | 1/1998 | Fitch et al. | |
| 6,297,626 B1 * | 10/2001 | Boston | G01N 15/0656 |
| | | | 324/204 |
| 6,392,562 B1 * | 5/2002 | Boston | G01N 15/0656 |
| | | | 324/204 |
| 2009/0051350 A1 | 2/2009 | Becker et al. | |
| 2010/0109686 A1 * | 5/2010 | Zhe | G01M 13/02 |
| | | | 324/698 |
| 2015/0108047 A1 * | 4/2015 | Rem | B03C 1/247 |
| | | | 209/555 |

\* cited by examiner

FLOW THROUGH DEBRIS SENSOR

CROSS-REFERENCE TO RELATED APPLICATION

This application claims the benefit of U.S. Provisional Patent Application No. 61/947,710, filed Mar. 4, 2014, which is hereby incorporated by reference as though fully set forth herein.

TECHNICAL FIELD

The present disclosure generally relates to an apparatus that may be configured to sense particles in a fluid medium. Sensed particles may include ferrous particles, conductive non-ferrous particles, and/or non-ferrous non-conductive particles.

BACKGROUND

Debris sensors may be used in one or more of a variety of applications, which may include lubrication systems. As components and/or machines that may be connected to a lubrication system break down, particles of the components and/or machines may break off and flow with lubrication fluid. Detecting and/or measuring particles or debris in lubrication fluid may be useful for evaluating the physical condition of the components connected to the lubrication system. For example, and without limitation, increased amounts of debris may indicate an imminent failure and preventative steps may be taken to avoid complete failure.

Previous designs relating to measuring particles include U.S. Pat. No. 5,028,318 (Aslin) which is assigned to the assignee of this application, and is hereby incorporated herein by reference in its entirety.

SUMMARY

An embodiment of a debris sensor according to teachings of the disclosure includes a body having a first end and a second end; a ferrous particle sensor connected to the body; a magnetic chip collector connected to the body at a position closer to the second end than the ferrous particle sensor; a plurality of magnets disposed closer to the second end than the magnetic chip collector; and a non-ferrous particle sensor connected to the body.

BRIEF DESCRIPTION OF THE DRAWINGS

Embodiments of the invention will now be described, by way of example, with reference to the accompanying drawings, wherein.

DETAILED DESCRIPTION

Reference will now be made in detail to embodiments of the present disclosure, examples of which are described herein and illustrated in the accompanying drawings. While the invention will be described in conjunction with embodiments, it will be understood that they are not intended to limit the present disclosure to these embodiments. On the contrary, the present disclosure is intended to cover alternatives, modifications and equivalents, which may be included within the spirit and scope of the present disclosure.

Figure 1:
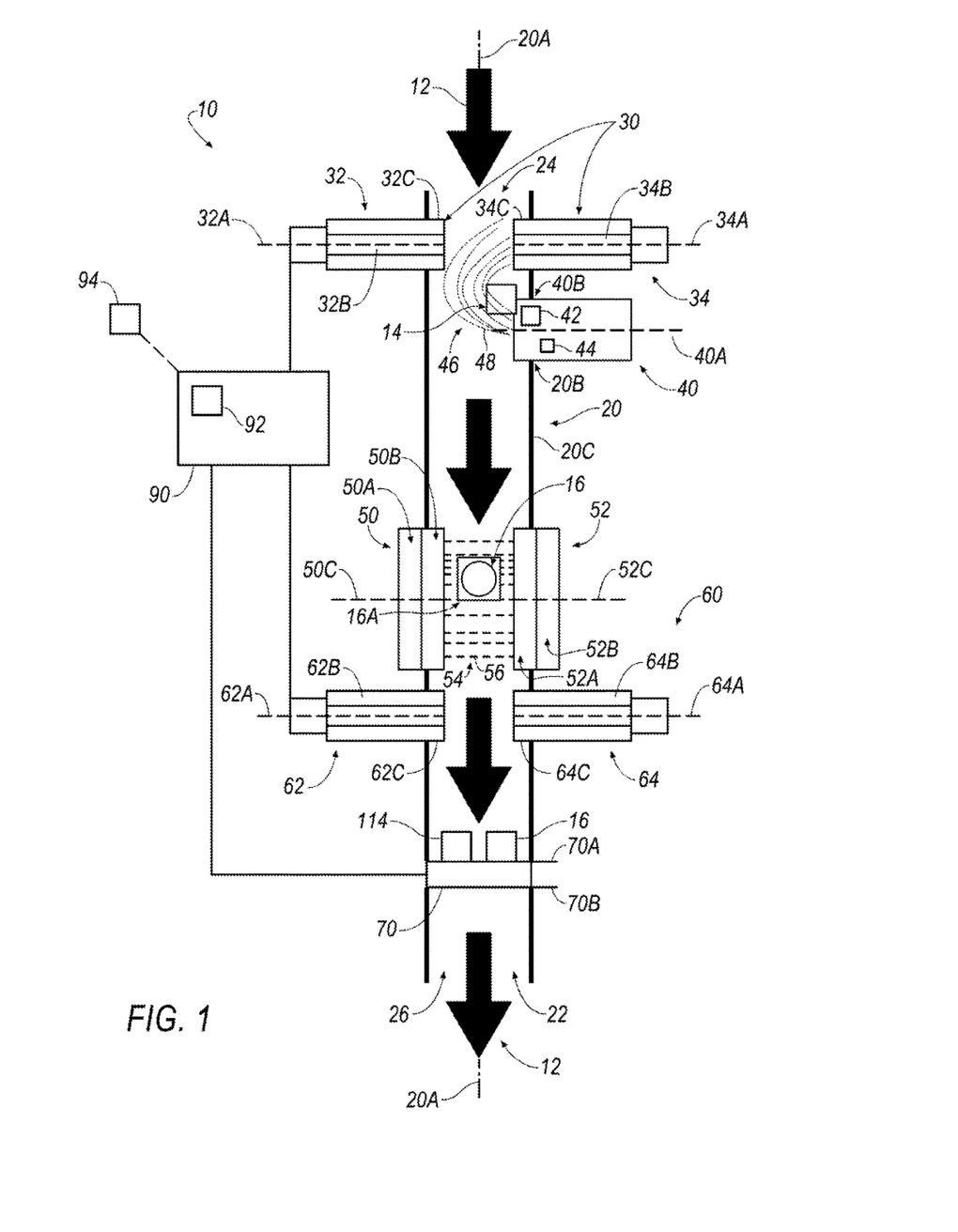
FIG. 1 is a cross-sectional view of an embodiment of a debris sensor shown generally in accordance with teachings of the disclosure.

Referring to FIG. 1, a debris sensor 10 may include a body 20, a first sensor 30, a collector 40, one or more magnets 50, 52, a second sensor 60, and/or an indicating screen 70. Debris sensor 10 may be configured for measuring and/or detecting particles, such as, for example, ferrous particles 14, non-ferrous conductive particles 16, and/or non-ferrous non-conductive particles 114 in a fluid 12. Additionally or alternatively, debris sensor 10 may be configured to capture and/or filter particles from fluid 12.

Body 20 may comprise one or more of a variety of shapes, sizes, and/or configurations. Body 20 may include a generally elongated shape and/or may be generally cylindrical. Body 20 may include a longitudinal and/or central axis 20A, an outer wall 20C, an inlet 24 at a first end and/or an outlet 26 at a second end. Body 20 may be configured to allow a fluid 12 to move between inlet 24 and outlet 26.

In embodiments, first sensor 30 may include a ferrous particle sensor. First sensor 30 may include one or more electrical conductors. An electrical conductor may comprise one or more of a variety of shapes, sizes, and/or configurations. In embodiments, an electrical conductor may include a coil, which may be a sensing coil. For example, and without limitation, first sensor 30 may include a first coil 32 and/or a second coil 34. A coil may be configured to sense changes in a magnetic field. For example, first coil 32 and/or second coil 34 may be disposed in and/or in proximity to magnetic field 46 and/or changes to magnetic field 46 may induce an electromotive force (EMF) and/or a voltage in first coil 32 and/or second coil 34.

In embodiments, first coil 32 and/or second coil 34 may comprise one or more of a variety of shapes, sizes, and/or configurations. For example, and without limitation, first coil 32 and/or second coil 34 may have a generally annular, cylindrical, and/or helical shape. First coil 32 may have a longitudinal axis 32A and/or second coil 34 may have a longitudinal axis 34A. First coil 32 and/or second coil 34 may include and/or be disposed around a core (e.g., cores 32B, 34B), which may include, for example, a metal and/or ferrite core. A core (e.g., cores 32B, 34B) may or may not be magnetic and/or may increase a sensitivity of a coil to the generation of and/or changes to a magnetic field.

In embodiments, first coil 32 and second coil 34 may be disposed in one or more of a variety of configurations. For example, and without limitation, longitudinal axis 32A of first coil 32 and/or longitudinal axis 34A of second coil 34 may be disposed generally perpendicular to axis 20A and/or to a direction of the flow of fluid 12 (which may be generally aligned with axis 20A). In embodiments, first coil 32 and/or second coil 34 may not be arranged concentrically with each other and/or concentrically with body 20. In embodiments, first coil 32 and second coil 34 may be disposed so that they are generally axially aligned with each other (e.g., axis 32A and axis 34A may be aligned with each other). In embodiments, a portion 32C of first coil 32 and/or a portion 34C of second coil 34 may extend through outer wall 20C of body 20.

Figure 2:
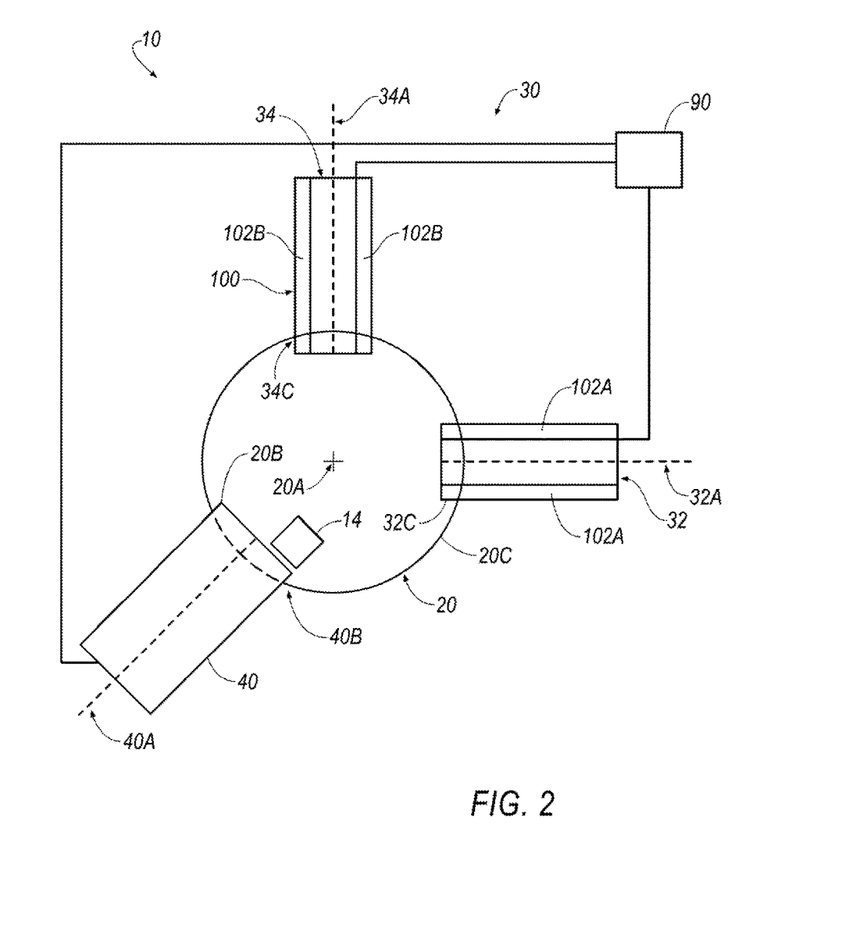
FIG. 2 is a cross-sectional view of an embodiment of a debris sensor shown generally in accordance with teachings of the disclosure.

As generally illustrated in FIG. 2, in embodiments, first coil 32 and second coil 34 may be circumferentially spaced from each other relative to axis 20A. For example, longitudinal axis 32A of first coil 32 may be circumferentially spaced (e.g., by about 90 degrees) from longitudinal axis 34A of second coil 34 relative to axis 20A. Circumferentially spaced coils (e.g., first coil 32 and/or second coil 34) may allow or provide for determining a three dimensional aspect of sensed particles. In embodiments, first sensor 30 may include a coil (e.g., first coil 32) that may generally be configured for measuring characteristics of one or more ferrous particles (e.g., ferrous particles 14) in two dimensions. For example, first coil 32 may be configured for measuring widths and lengths of ferrous particles 14. Additionally or alternatively, first sensor may include a coil (e.g., second coil 34) that may generally be configured for measuring characteristics of ferrous particles (e.g., ferrous particle 14) in two dimensions, at least one of which may be different than one of the two dimensions that may be measured by first coil 32. For example and without limitation, second coil 34 may be configured for measuring a height and a length of ferrous particles 14. In embodiments, first sensor 30 may include first coil 32 and second coil 34 that may be circumferentially spaced from each other relative to axis 20A, which may allow first sensor 30 to measure a size of ferrous particle 14 in three dimensions (e.g., length, width, and height).

In embodiments, debris sensor 10 may be configured to reduce and/or minimize a saturation limit effect and/or increase a saturation limit relative to conventional debris sensors. A saturation limit may correspond to an amount and/or concentration of particles (e.g., ferrous particles 14) in fluid 12 at which sensor functionality may begin to degrade because the particles may at least partially cover a coil of a sensor. In embodiments, first coil 32 and/or second coil 34 may be configured to not attract ferrous particles 14 and/or to attract relatively few ferrous particles 14. For example, first coil 32 and/or second coil 34 may include relatively few magnetic portions, may not include any magnetic portions, may include magnetic portions that are sufficiently far away from flowing ferrous particles 14 so the particles are not attracted, and/or may include magnetic portions that are sufficiently covered and/or shielded to not attract ferrous particles 14. Attracting relatively few and/or not attracting substantially any ferrous particles 14 may reduce and/or prevent a buildup of ferrous particles 14 on or near a coil (e.g., coil 32 and/or coil 34), which may increase a saturation limit of debris sensor 10 relative to conventional sensors. A buildup of ferrous particles 14 on a coil may interfere with a voltage induced in a coil and/or may reduce the accuracy and/or precision of a debris measurement.

As generally illustrated in FIGS. 1 and 2, in embodiments, debris sensor 10 may include a collector 40. Collector 40 may be disposed on and/or in body 20, and/or may be connected to body 20. Collector 40 may include a longitudinal axis 40A. In embodiments, collector 40 may include a threaded portion 40B that may correspond to a threaded portion of body 20, and which may permit collector 40 to be fastened to body 20 (e.g., aperture 20B may be threaded and/or configured to receive threaded portion 40B). Collector 40 may include a chip collector, which may include a magnetic chip collector. Collector 40 may be configured to capture particles (e.g., ferrous particles 14) and/or may include a magnet 42 that may comprise a magnetic material, such as, without limitation, samarium-cobalt and/or neodymium. Additionally or alternatively, magnet 42 may include an electromagnet and/or any material that may include magnetic properties.

In embodiments, collector 40 may be configured to be removed and/or may permit evaluation of captured particles (e.g., ferrous particles 14 that may have been captured). Collector 40 may be configured to be removed during system 18 operation (e.g., without shutting a system 18 down for maintenance) and/or may include a feature 44, such as self-closing feature and/or valve, that may be configured to prevent fluid 12 from leaking out through collector 40 and/or through aperture 20B in body 20.

As generally illustrated in FIG. 1, collector 40 may be disposed downstream of and/or closer to outlet 26 than first sensor 30, and/or collector 40 may be disposed between first sensor 30 and second sensor 60. Collector 40 may be connected to a different portion of body 20 than first sensor 30 and/or collector 40 may be configured to operate partially and/or completely independently of first sensor 30 (e.g., collector 40 may be configured to operate in substantially the same manner in embodiments with a first sensor 30 and in embodiments without a first sensor 30). Collector 40 may comprise one or more of a variety of shapes, sizes, and/or configurations. Collector 40 may or may not be disposed generally axially aligned with first coil 32 and/or second coil 34, and/or collector 40 may be circumferentially spaced from first coil 32 and/or second coil 34 relative to axis 20A. As generally illustrated in FIG. 2, for example, and without limitation, axis 40A of collector 40 may extend radially outward relative to axis 20A at an angle of about 135 degrees from axis 32A of first coil 32 in a first direction and/or at an angle of about 135 degrees from axis 34A of second coil 34 in a second (e.g., opposite) direction.

In embodiments, such as generally illustrated in FIG. 1, collector 40 may be configured as a source of a magnetic field 46 that may extend at least partially within body 20. Magnetic field 46 may, for purposes of general representation, correspond to magnetic field lines 48, such as generally illustrated in FIG. 1. In embodiments, magnetic field 46 may be configured to be monitored by a first sensor 30. For example, first coil 32 and/or second coil 34 of first sensor 30 may be configured such that changes in magnetic field 46 may induce a voltage and/or an electromotive force (EMF) in first coil 32 and/or second coil 34.

In embodiments, first sensor 30 may be configured to cooperate with collector 40 to detect ferrous particles 14 in fluid 12. For example, and without limitation, if fluid 12 includes ferrous particles 14 and fluid 12 enters body 20, ferrous particles 14 may enter magnetic field 46. As ferrous particles 14 move in magnetic field 46, properties of magnetic field 46 may be altered. Alterations of a magnetic field 46 may result in an induced electromotive force (EMF) and/or a induced voltage in a conductor in proximity to the magnetic field 46, such as, for example, first coil 32 and/or second coil 34 of first sensor 30. An induced EMF and/or voltage may be large enough and/or first sensor 30 may be sufficiently sensitive enough for first sensor 30 to detect and/or measure the induced EMF and/or generated voltage. Measured induced EMFs and/or voltages may correspond to various characteristics (e.g., sizes, masses, etc.) of ferrous particles 14 of fluid 12.

In embodiments, collector 40 may be disposed sufficiently downstream of and/or closer to outlet 26 than first sensor 30, such that ferrous particles 14 do not build up on first sensor and/or may build up on, in, and/or near collector 40 without substantially affecting the function of first sensor 30.

In embodiments, debris sensor 10 may include one or more magnets (e.g., a first magnet 50 and/or a second magnet 52) that may be disposed downstream of and/or closer to outlet 26 than first sensor 30 and/or collector 40. First magnet 50 may be connected to body 20 and/or may be disposed at least partially within body 20. Additionally or alternatively, a second magnet 52 may be connected to body 20 and/or may be disposed at least partially within body 20. First magnet 50 and second magnet 52 may be spaced (e.g., circumferentially) from each another and/or axis 50C of first magnet 50 and axis 52C of second magnet 52 may extend radially outwardly at an angle relative to each other. For example, and without limitation, axis 50C of a first magnet 50 may extend radially outwardly at an angle of about 180 degrees from axis 52C of a second magnet 52. In embodiments including more than one magnet, magnets (e.g., a first magnet 50 and/or a second magnet 52) may cooperate and/or may be disposed such that a magnetic field (e.g., magnetic field 54) exists between two or more magnets. For example, and without limitation, first magnet 50 may include a north pole 50A that may be generally directed away from an internal space 22 of body 20 (e.g., radially outward relative to axis 20A), first magnet 50 may include a south pole 50B that may be generally directed toward space 22 (e.g., radially inward relative to axis 20A toward a center of body 20), second magnet 52 may include a south pole 52B that may be generally directed away from space 22 (e.g., radially outward relative to axis 20A), and/or second magnet 52 may include a north pole 52A that may be generally directed toward space 22 (e.g., radially inward relative to axis 20A). Magnetic field 54 may exist at least between south pole 50B and north pole 52A and/or may correspond to magnetic field lines 56.

In embodiments, magnetic field 54 may be configured to induce eddy currents in conductive particles 16 that may move through magnetic field 54. Eddy currents in conductive particles 16 may result in conductive particles 16 corresponding to magnetic fields 16A of their own, even if the conductive particles 16 do not include magnetic materials and/or are non-ferrous.

In embodiments, first magnet 50 and/or second magnet 52 may be axially spaced and/or shielded from first sensor 30 and/or collector 40. For example, and without limitation, first and second magnets 50, 52 may be sufficiently axially spaced and/or shielded from collector 40 such that magnetic field 46 and magnetic field 54 do not affect or do not substantially affect each other.

In embodiments, debris sensor 10 may include second sensor 60. Second sensor 60 may comprise one or more of a variety of shapes, sizes, and/or configurations. In embodiments, second sensor 60 may be axially spaced and/or shielded from first sensor 30 and/or collector 40. For example, and without limitation, second sensor 60 may be sufficiently axially spaced and/or shielded from collector 40 such that second sensor 60 is not affected or is not significantly affected by magnetic field 46. In embodiments, second sensor 60 may be disposed downstream of and/or closer to outlet 26 than first sensor 30, collector 40, first magnet 50, and/or second magnet 52.

In embodiments, second sensor 60 may be configured to sense particles, such as, for example, non-ferrous and/or conductive particles 16. Second sensor 60 may be referred to herein as non-ferrous particle sensor 60. Second sensor 60 may include one or more electrical conductors. An electrical conductor may comprise one or more of a variety of shapes, sizes, and/or configurations. In embodiments, an electrical conductor may include a coil (e.g., first coil 62 and/or second coil 64).

First coil 62 and/or second coil 64 may be configured to sense magnetic fields 16A that correspond to eddy currents induced in conductive particles 16. For example, first coil 62 and/or second coil 64 may be disposed in proximity to magnetic fields 16A, and/or generation of and/or changes to magnetic fields 16A may induce an electromotive force (EMF) and/or a voltage in first coil 62 and/or second coil 64.

In embodiments, a first coil 62 and/or a second coil 64 may comprise one or more of a variety of shapes, sizes, and/or configurations. For example, and without limitation, first coil 62 and/or second coil 64 may include a generally annular, cylindrical, and/or helical shape. First coil 62 may include a portion 62C that may at least partially extend into space 22 and/or second coil 64 may include a portion 64C that may at least partially extend into space 22. First coil 62 may include longitudinal axis 62A and/or second coil 64 may include longitudinal axis 64A. In embodiments, longitudinal axis 62A of first coil 62 and/or longitudinal axis 64A of second coil 64 may be disposed generally perpendicular to axis 20A and/or first coil 62 and second coil 64 may be disposed so that they are generally axially aligned with each other along body 20. First coil 62 and/or second coil 64 may include and/or be disposed around a core (e.g., cores 62B, 64B), which may include, for example, a metal and/or ferrite core. Core 62B and/or core 64B may or may not include magnetic material and/or may increase a sensitivity of a coil. For example, and without limitation, core 62B may increase the sensitivity of first coil 62 to generation of and/or changes to magnetic fields 16A, and/or core 64B may increase the sensitivity of second coil 64 to generation of and/or changes to magnetic fields 16A. Coils including an increased sensitivity to generation of and/or changes to magnetic fields may allow debris sensor 10 to include increased sensitivity to conductive particles 16, which may correspond to being able to detect and/or measure smaller particles, and/or may allow for more accurate and/or precise measurements of particles 16.

Figure 3:
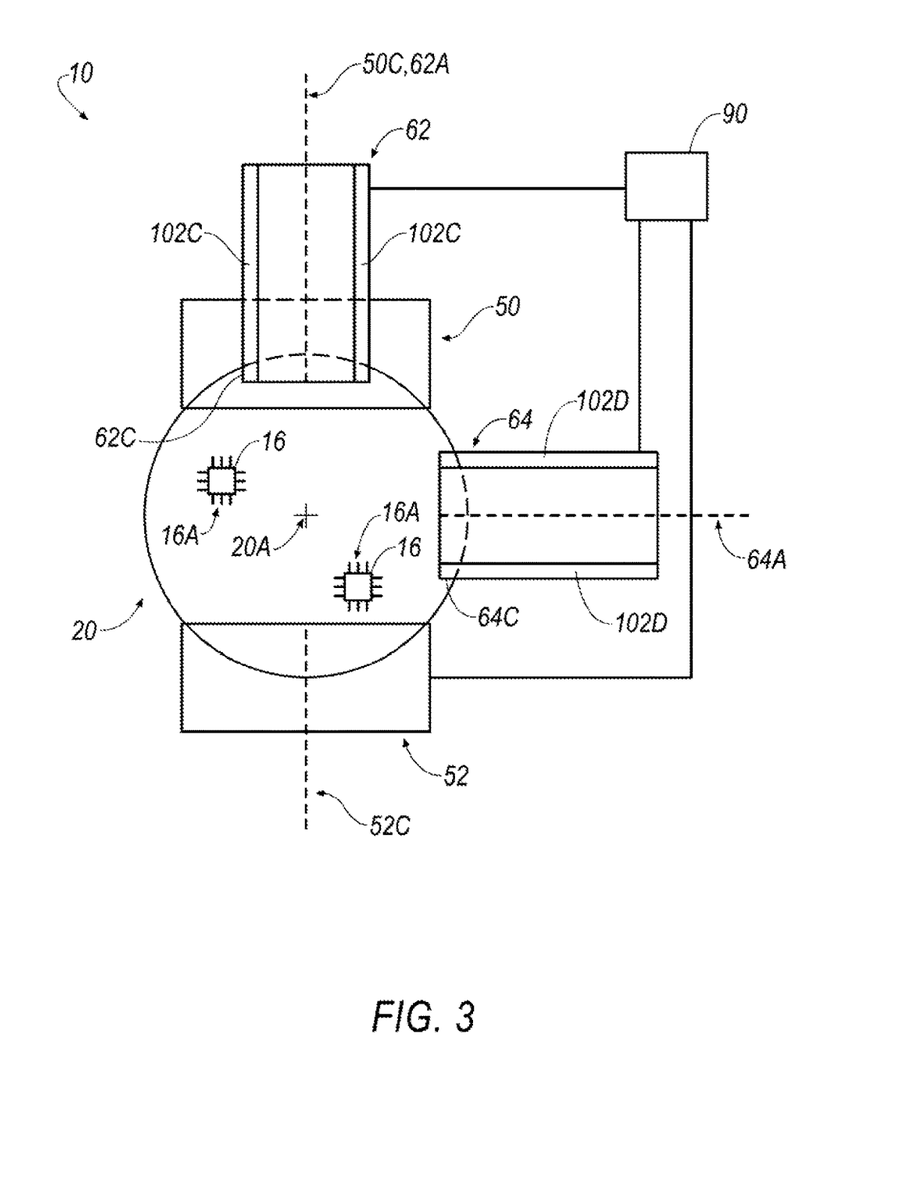
FIG. 3 is a cross-sectional view of an embodiment of a debris sensor shown generally in accordance with teachings of the disclosure.

In embodiments, first coil 62 and/or second coil 64 may be disposed in one or more of a variety of configurations. As generally illustrated in FIG. 3, in embodiments, first coil 62 and second coil 64 may be circumferentially spaced from each other relative to axis 20A. For example, and without limitation, longitudinal axis 62A of first coil 62 may extend radially outward relative to axis 20A at angle of about 90 degrees from longitudinal axis 64A of second coil 64, which may allow debris sensor 10 to measure conductive particles 16 in three dimensions. In embodiments, first coil 62 and/or second coil 64 may be disposed generally circumferentially aligned with first magnet 50 and/or second magnet 52. For example, first coil 62 may be circumferentially aligned with first magnet 50, second magnet 52 may be circumferentially spaced from first coil 62 and first magnet 50 by about 180 degrees, and/or second coil 64 may be circumferentially spaced from first coil 62 and first magnet 50 by about 90 degrees in one direction and/or circumferentially spaced from second magnet 52 by about 90 degrees in another (e.g., opposite) direction.

In embodiments, second sensor 60 may be configured to cooperate with first magnet 50 and/or second magnet 52 to sense and/or detect conductive particles 16. For example, if conductive particles 16 enter magnetic field 54, eddy currents may be induced in conductive particles 16, which may result in the generation of and/or changes to magnetic fields 16A corresponding to conductive particles 16. Magnetic fields 16A of conductive particles 16 may create and/or change a voltage and/or EMF induced in first coil 62 and/or in second coil 64. A degree of change in an induced voltage or EMF may correspond to a measure of conductive particles 16, such as, for example, a mass and/or size of conductive particles 16. In embodiments, first coil 62 and second coil 64 may be configured for measuring conductive particles 16 in three dimensions, such as, for example, length, width, and height dimensions of conductive particles 16.

In embodiments, debris sensor 10 may include a screen 70. Screen 70 may be connected to and/or disposed at least partially in body 20. Screen 70 may be disposed downstream of first sensor 30, collector 40, magnets 50, 52, and/or second sensor 60. Screen 70 may be configured to capture particles, such as, for example, particles that may not have been captured by collector 40, which may include non-ferrous and/or conductive particles 16. In embodiments, screen 70 may be configured to be removed from debris sensor 10 and/or body 20 and/or may configured such that captured particles (e.g., conductive particles 16 that may have been captured) may be removed, for example, during a maintenance process of system 18.

In embodiments, screen 70 may include an indicator screen and/or screen 70 may be configured to provide an indication of the presence of particles, such as, for example, conductive particles 16, which may be non-ferrous. Screen 70 may include an electrical resistance in the absence of conductive particles 16 and/or an electrical resistance of screen 70 may change if conductive particles 16 contact screen 70. For example, and without limitation, conductive particles 16 may come into contact with screen 70 and/or conductive particles 16 may close previously open electrical circuits, which may change a resistance of screen 70. Debris sensor 10 may be configured to monitor the resistance of screen 70 for changes and/or to detect the presence of conductive particles 16 if a change in resistance is greater than a given threshold.

In embodiments, screen 70 may be configured to provide an indication of the presence of non-ferrous non-conductive particles 114. Non-ferrous non-conductive particles 114 may, for example, include ceramic particles that may originate from a ceramic bearing that may be used by a machine 18C of system 18 (see, e.g., FIG. 6). Screen 70 may include a capacitance, which may include being configured as a parallel plate capacitor having a capacitance. For example, and without limitation, screen 70 may include a first plate 70A that may be upstream (e.g., closer to inlet 24) of a second plate 70B. If non-ferrous non-conductive particles 114 reach screen 70, the non-ferrous non-conductive particles 114 may alter the characteristics of the matter between plates 70A, 70B of screen 70 (e.g., change dielectric characteristics) and/or alter the capacitance of screen 70. A change in capacitance may correspond to an amount of non-ferrous non-conductive particles 114 present at screen 70. Debris sensor 10 may be configured to monitor the capacitance of screen 70 for changes and/or to detect the presence of non-ferrous non-conductive particles 114 if a change in capacitance is greater than a given threshold. In embodiments, portions of screen 70 (e.g., upstream plate 70A) may be electrically insulated, which may reduce or eliminate the effect on the capacitance of screen 70 if a ferrous particle 14 and/or a conductive non-ferrous particle 16 contacts screen 70.

Figure 4:
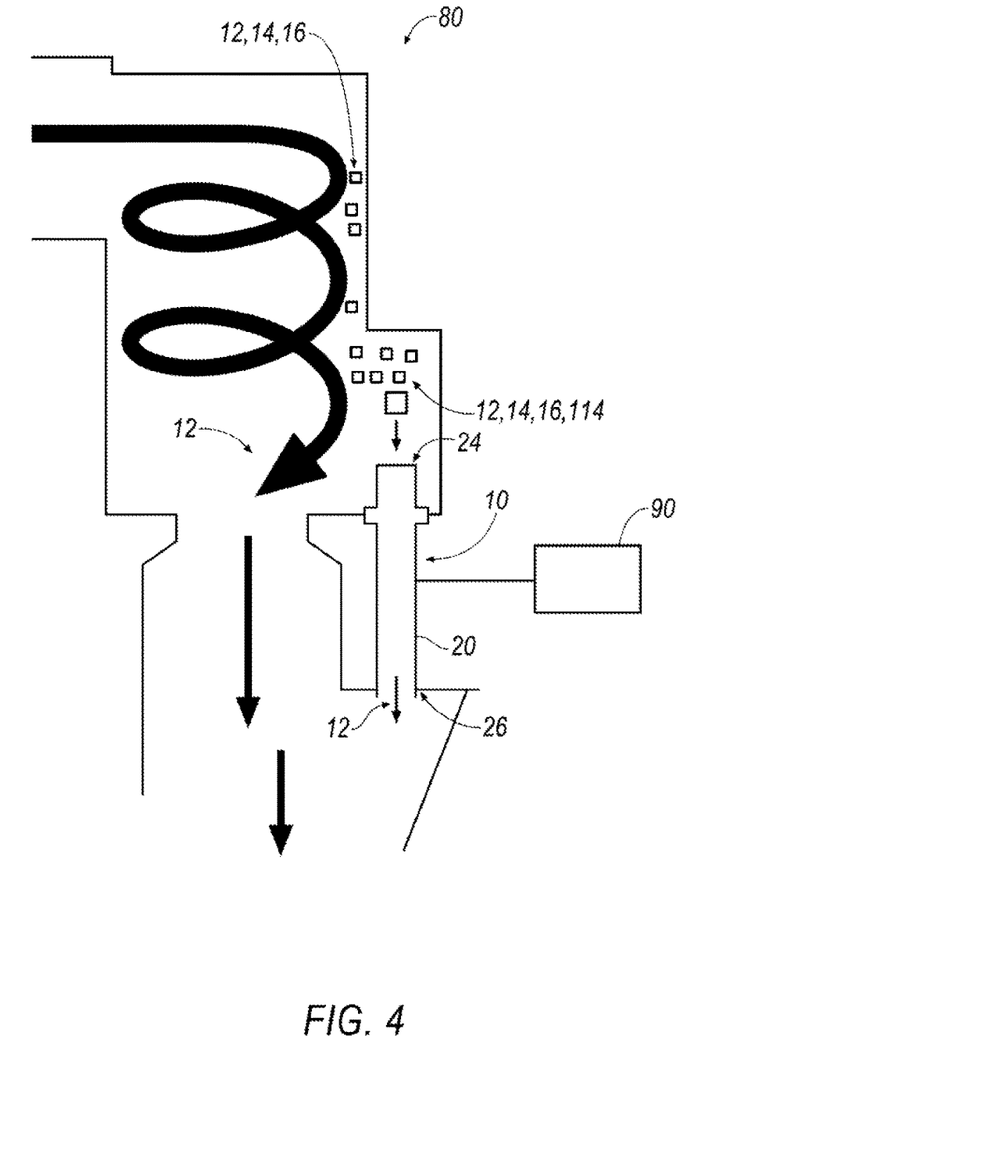
FIG. 4 is a cross-sectional view of another embodiment of a debris sensor and a particle separator shown generally in accordance with teachings of the disclosure.

In embodiments, such as generally illustrated in FIGS. 1, 3, and 4, screen 70 may be configured to capture particles (e.g., ferrous particles 14 not captured by collector 40, conductive particles 16, non-ferrous non-conductive particles 114, etc.) to allow fluid 12 to pass through, and/or may be configured as a filter. For example, and without limitation, debris sensor 10 may capture via collector 40 some or all of any ferrous particles 14 that enter debris sensor 10 at inlet 24, and/or debris sensor 10 may capture and/or filter via screen 70 some or all of any other particles (e.g., conductive particles 16) and/or ferrous particles 14 not captured by collector 40 that may enter debris sensor 10. Debris sensor 10 may allow filtered fluid 12 to exit debris sensor 10 at outlet 26.

In embodiments, such as generally illustrated in FIGS. 1 and 4, debris sensor 10 may include and/or may be configured to be connected to a monitoring unit 90. Monitoring unit 90 may include a programmable microprocessor and/or microcontroller, and/or may include, for example, an application specific integrated circuit (ASIC). Monitoring unit 90 may include a central processing unit (CPU), memory, and/or an input/output (I/O) interface. Monitoring unit 90 may be configured to perform various functions with appropriate programming instructions and/or code embodied in software, hardware, and/or other medium.

In embodiments, monitoring unit 90 may include a Quantitative Debris Monitor (QDM) that may be digital. Monitoring unit 90 may be configured to monitor one or more sensors (e.g., first sensor 30 and/or second sensor 60), a collector (e.g., collector 40), and/or a screen (e.g., screen 70). Monitoring unit 90 may be configured to receive signals and/or data from sensors (e.g., first sensor 30 and/or second sensor 60), collectors (e.g., collector 40), and/or screens (e.g., screen 70) to determine and/or calculate one or more characteristics of particles that may flow into debris sensor inlet 24. For example, and without limitation, monitoring unit 90 may be configured to calculate a size of a ferrous particle 14 according to a voltage signal received/output from first sensor 30 and/or calculate a size of a non-ferrous particle 16 according to a voltage signal received/output from second sensor 60. Additionally or alternatively, monitoring unit 90 may be configured to determine a status of system 18 according to characteristics of particles (e.g., ferrous particles 14 and/or conductive particles 16) that may flow into debris sensor inlet 24. For example, and without limitation, monitoring unit 90 may be configured to indicate an imminent and/or an actual failure of a component of system 18 if a characteristic of sensed particles is outside of a predetermined range and/or exceeds a predetermined threshold (e.g., monitoring unit 90 senses that too many particles are present in fluid 12 and/or the particles in fluid 12 are too large). A predetermined range and/or a predetermined threshold may correspond to a normal/expected amount of particles and/or may be configured to reduce or prevent false alarms.

In embodiments, such as generally illustrated in FIG. 1, monitoring unit 90 may include and/or be connected to a communication device 92. Communication device 92 may permit monitoring unit to communicate via a wired and/or wireless network to a remote location 94. For example, and without limitation, communication device 92 may permit monitoring unit 90 to provide an indication of an imminent and/or actual failure to a remote location 94.

In embodiments, such as generally illustrated in FIGS. 2 and 3, a sensor (e.g., first sensor 30 and/or second sensor 60) may include a built-in-test (BIT) system 100. A BIT system 100 may be configured to test a function of first sensor 30 and/or second sensor 60. BIT system 100 may include a test coil (e.g., test coils 102A, 102B, 102C, 102D) disposed in first sensor 30 and/or test coil 102 may be in proximity to and/or wrapped around a primary coil (e.g., first coil 32, second coil 34, first coil 62, and/or second coil 64). BIT system 100 may be configured to provide a test signal via a test coil to a primary coil of a sensor. For example, and without limitation, test coil 102A may be configured to test first coil 32, test coil 102B may be configured to test second coil 34, test coil 102C may be configured to test first coil 62, and/or test coil 102D may be configured to test second coil 64. A test signal may be configured to simulate the presence of ferrous particles 14 and/or conductive particles 16 in fluid 12. The response of a primary coil (e.g., coils 32, 34, 62, 64) to the test signal may be evaluated to assess the accuracy and/or precision of a primary coil. BIT system 100 may include an automatic BIT, which may be automatically activated if debris sensor 10, first sensor 30, and/or second sensor 60 is turned on, started up, and/or connected to a monitoring unit 90. Additionally or alternatively, BIT system 100 may be configured to allow a user to initiate a BIT at any time.

Figure 5:
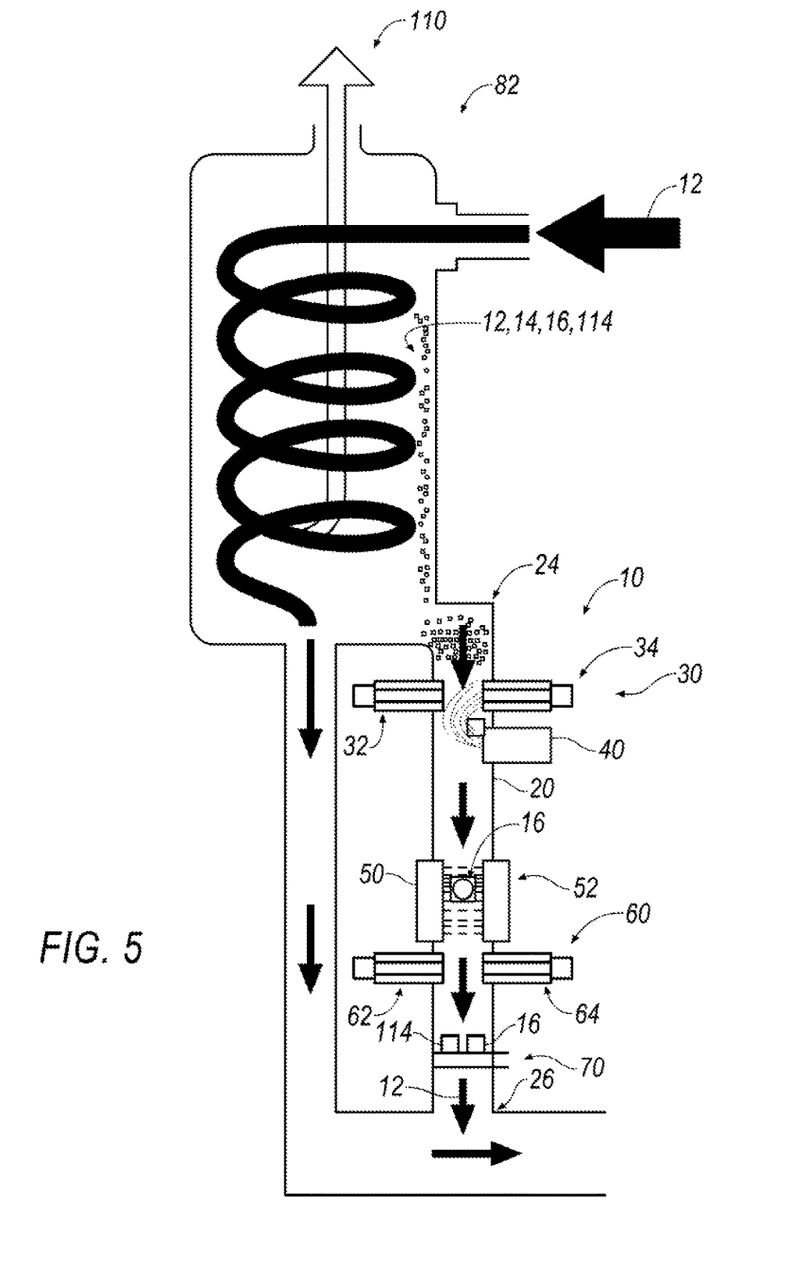
FIG. 5 is a cross-sectional view of another embodiment of a debris sensor and a particle separator shown generally in accordance with teachings of the disclosure.

In embodiments, such as generally illustrated in FIGS. 4 and 5, body 20 may be disposed such that inlet 24 and/or outlet 26 may be in fluid connection with a particle separator, such as, for example, a cyclonic particle separator (e.g., particle separator 80 and/or particle separator 82). Particle separators 80, 82 may be configured to generally separate and/or concentrate particles in a volume of fluid (e.g., fluid 12) and direct them toward body 20. Body 20 may be disposed such fluid 12, which may include particles, may be directed from a particle separator 80, 82 toward inlet 24 and/or fluid 12 that has passed through body 20 may exit through outlet 26 and/or mix with fluid exiting the separator. Particle separators (e.g., particle separator 82) may, additionally or alternatively, be configured to separate air 110 from fluid 12, for example, as generally illustrated in FIG. 5.

Figure 6:
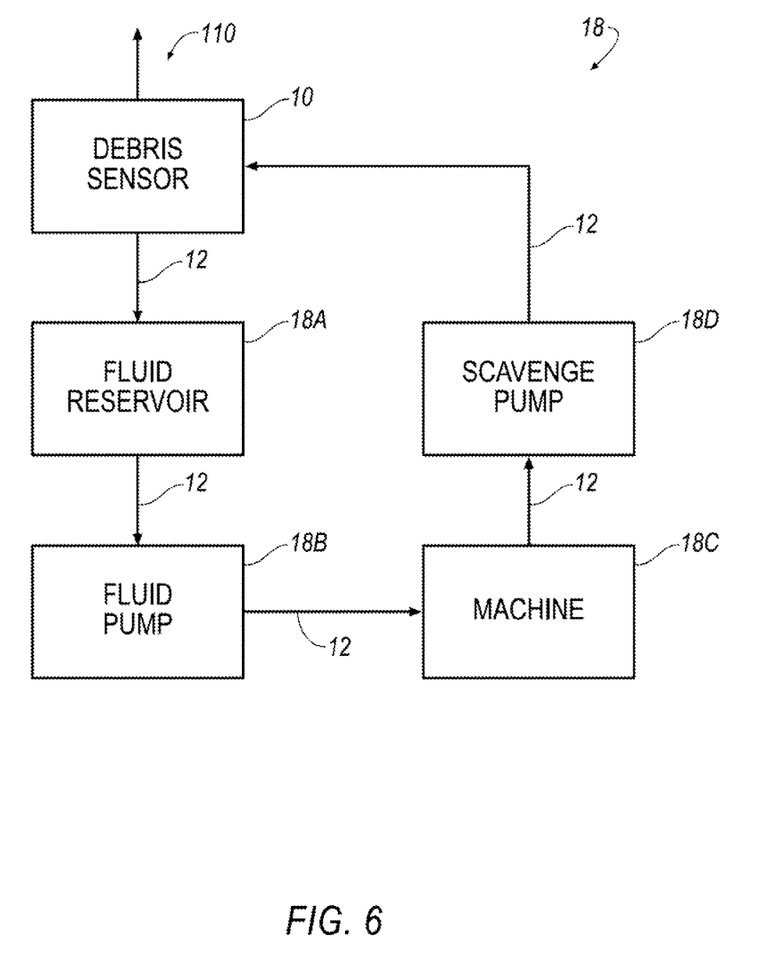
FIG. 6 is a schematic view of an embodiment of debris sensor connected to a system shown generally in accordance with teachings of the disclosure.

As generally illustrated in FIG. 6, in embodiments, debris sensor 10 may be connected to a system 18, which may include a fluid reservoir 18A, a fluid pump 18B, a component and/or machine 18C in which fluid may be used, and/or a scavenge pump 18D. Debris sensor 10 may be configured to sense debris in fluid 12 received from scavenge pump 18D and/or provide filtered fluid to fluid reservoir 18A. In embodiments, debris sensor 10 may be disposed in an inline configuration in which all fluid 12 of system 18 flows through debris sensor, and/or debris sensor 10 may be disposed in a bypass configuration in which some of fluid 12 of system 18 flows through debris sensor 10 and some of fluid 12 does not flow through debris sensor 10. For example, and without limitation, all of fluid 12 may enter a particle separator 80, 82 (see, e.g., FIGS. 4 and 5), and some of that fluid 12 may flow directly through particle separator 80, 82 back into a main fluid path of system 18, and some of fluid 12 may flow through debris sensor 10 before flowing back into the main fluid path of system 18.

In embodiments, debris sensor 10 may be configured as a passive debris sensor. For example, and without limitation, in embodiments, a debris sensor 10 may be configured without a signal generator and/or oscillator, may not consume electrical energy, and/or may not be connected to electrical power source.

The foregoing descriptions of specific embodiments of the present disclosure have been presented for purposes of illustration and description. They are not intended to be exhaustive or to limit the present disclosure to the precise forms disclosed, and various modifications and variations are possible in light of the above teaching. For example, and without limitation, it should be understood that references to a coil are not limited to a specific shape and/or configuration. The embodiments were chosen and described in order to explain the principles of the invention and its practical application, to thereby enable others skilled in the art to utilize the present disclosure and various embodiments with various modifications as are suited to the particular use contemplated. It is intended that the scope of the present disclosure be defined by the claims and their equivalents.

What is claimed:

1. A debris sensor, comprising:
   a body including a first end and a second end;
   a ferrous particle sensor connected to the body;
   a magnetic chip collector connected to the body at a position closer to the second end than the ferrous particle sensor;
   a plurality of magnets disposed closer to the second end than the magnetic chip collector; and
   a non-ferrous particle sensor connected to the body;
   wherein the magnetic chip collector is configured to generate a magnetic field and to attract ferrous particles, and the ferrous particle sensor is configured to sense changes in the magnetic field generated by the magnetic chip collector caused by the ferrous particles.

2. The debris sensor of claim 1, comprising a removable indicator screen downstream of the non-ferrous particle sensor.

3. The debris sensor of claim 1, wherein a sensing coil of the non-ferrous particle sensor is configured to sense magnetic fields generated by eddy currents created in non-ferrous particles as the non-ferrous particles flow through a magnetic field created by the plurality of magnets.

4. The debris sensor of claim 1, wherein the plurality of magnets includes a first magnet with a south pole directed toward a center of the body and a second magnet with a north pole directed toward the center of the body.

5. The debris sensor of claim 1, wherein the ferrous particle sensor includes a pair of sensing coils.

6. The debris sensor of claim 5, wherein the pair of sensing coils are disposed about 90 degrees apart from each other.

7. The debris sensor of claim 1, wherein the ferrous particle sensor includes a sensing coil disposed perpendicularly to a longitudinal axis of the body.

8. The debris sensor of claim 1, wherein the ferrous particle sensor includes a sensing coil that includes a longitudinal axis aligned perpendicularly to a longitudinal axis of the body.

9. The debris sensor of claim 1, comprising a built-in-test system configured to generate a test signal to simulate a ferrous particle and/or a non-ferrous conductive particle being in proximity to the ferrous particle sensor and the non-ferrous particle sensor.

10. The debris sensor of claim 1, wherein the ferrous particle sensor is configured to output signals to be processed by a digital quantitative debris monitor.

11. The debris sensor of claim 1, wherein the debris sensor is configured to be connected to a particle separator.

12. The debris sensor of claim 11, wherein the particle separator includes a cyclonic particle separator.

13. The debris sensor of claim 1, wherein the body includes an inlet and an outlet, and wherein body is configured to receive particle-filled fluid at its inlet.

14. The debris sensor of claim 1, wherein the ferrous particle sensor includes a first coil and a second coil; the first coil and the second coil are circumferentially spaced from each other by about 90 degrees; the magnetic chip collector is circumferentially spaced from the first coil by about 135 degrees in a first direction; and, the magnetic chip collector is circumferentially spaced from the second coil by about 135 degrees in a second direction.

15. A debris sensor, comprising:
a first sensor;
a source of a first magnetic field disposed downstream of the first sensor, the first magnetic field configured to be sensed by the first sensor;
a second sensor disposed downstream of the source of the first magnetic field; and
a source of a second magnetic field disposed upstream of the second sensor, the second magnetic field configured to be sensed by the second sensor;
wherein the first sensor is configured to sense particles of a first type when the particles of a first type cause changes in the first magnetic field, the second sensor is configured to sense particles of a second type, and the debris sensor is configured to provide fluid communication from its inlet to its outlet.

16. The debris sensor of claim 15, wherein the first type of particles includes ferrous particles and the second type of particles includes non-ferrous conductive particles.

17. The debris sensor of claim 15, wherein the source of the first magnetic field includes a magnetic chip collector.

18. The debris sensor of claim 15, wherein the source of the second magnetic field includes a plurality of magnets.

19. The debris sensor of claim 17, wherein the magnetic chip collector is disposed at a sufficient distance downstream from the first sensor such that particles that have been collected by the magnetic chip collector do not impair operation of the first sensor.

20. The debris sensor of claim 18, wherein the second sensor includes a first coil and a second coil; the first coil is circumferentially aligned with a first magnet of the plurality of magnets; the second coil is circumferentially spaced from the first coil and the first magnet by about 90 degrees in a first direction; and, the second coil is circumferentially spaced from a second magnet of the plurality of magnets by about 90 degrees in a second direction.

21. The debris sensor of claim 15, comprising a capacitive indicating screen configured to sense non-ferrous non-conductive particles.

22. The debris sensor of claim 21, where the non-ferrous non-conductive particles include ceramic particles.

* * * * *